United States Patent
Lee et al.

(10) Patent No.: US 6,483,584 B1
(45) Date of Patent: Nov. 19, 2002

(54) DEVICE FOR MEASURING THE COMPLEX REFRACTIVE INDEX AND THIN FILM THICKNESS OF A SAMPLE

(75) Inventors: Solomon J. H. Lee, Taipei (TW); Chih-Kung Lee, Taipei (TW); Shu-Sheng Lee, Taipei (TW); Yang Yun-Chang, Taipei Hsien (TW); Lin Chan-Ching, Taipei (TW); Shuen-Chen Shiue, Keelung (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/549,738

(22) Filed: Apr. 14, 2000

(51) Int. Cl.[7] ................................... G01J 4/00
(52) U.S. Cl. ....................................... 356/369
(58) Field of Search ................. 356/368, 369, 356/364, 365, 366, 367; 250/225

(56) References Cited

U.S. PATENT DOCUMENTS

| | | | |
|---|---|---|---|
| 5,017,012 A | * 5/1991 | Merritt, Jr. et al. | 356/371 |
| 5,298,973 A | * 3/1994 | Fukazawa et al. | 356/368 |
| 5,910,842 A | * 6/1999 | Piwonka-Corle et al. | 356/369 |
| 6,134,011 A | * 10/2000 | Klein et al. | 356/369 |
| 6,191,846 B1 | * 2/2001 | Opsal et al. | 356/72 |
| 6,256,097 B1 | * 7/2001 | Wagner | 356/369 |
| 6,288,841 B1 | * 9/2001 | Lee et al. | 359/618 |

* cited by examiner

*Primary Examiner*—Michael P. Stafira
(74) *Attorney, Agent, or Firm*—J.C. Patents

(57) ABSTRACT

An ellipsometer for measuring the complex refractive index of a sample and thin film thickness according to the invention. The ellipsometer includes a linear polarized light source, a reference analyzer, a polarization analyzer and a light direction controller. The linear polarized light source used to generate a measuring beam for detecting the sample. The phase modulator used to control the phase of the measuring beam thereby to generate a sampling beam. The reference analyzer used to generate a reference beam according to part of the sampling beam thereby to adjust the intensity of the sampling beam. The polarization analyzer used to analyze the phase, polarization and intensity of the sampling beam after the sampling beam is reflected by the sample. The light direction controller used to control the angle and direction of the sampling beam with respect to the sample, wherein the sampling beam is reflected by the sample to enter the light direction controller, and thereafter the sampling beam is reflected by the light direction controller and re-reflected by the sample to enter the polarization analyzer along an original optical path, but toward an opposite direction.

52 Claims, 6 Drawing Sheets

DEVICE FOR MEASURING THE COMPLEX REFRACTIVE INDEX AND THIN FILM THICKNESS OF A SAMPLE

BACKGROUND OF THE INVENTION

1. Field of the Invention

The invention relates to an ellipsometer for measuring the complex refractive index and thin film thickness of a sample.

2. Description of the Related Art

Currently, only ellipsometer widely applied in semiconductor, optical and chemical industries can measure the complex refractive index and thin film thickness of a sample with better precision and higher resolution. Ellipsometer which has been developed over 100 years includes null ellipsometer, rotating-polarizer ellipsometer, rotating-analyzer ellipsometer, rotating-compensator ellipsometer, phase-modulation ellipsometer, small-modulation ellipsometer, dual-modulation ellipsometer, analyzer-shifting ellipsometer, compound-splitting ellipsometer, phase-shifting ellipsometer, and phase-analysis ellipsometer.

The principle of the ellipsometer is based on the ellipsomeric polarizing optics. Typically, a planar wave electric field E can be divided into two electric fields $E_p$ and $E_s$. That is, the planar wave electric field E can be expressed by:

$$\vec{E} = \vec{E}_p + \vec{E}_s \quad (1)$$

With Jones' vector, the electric field E can also be expressed by:

$$\vec{E} = \begin{bmatrix} E_p \\ E_s \end{bmatrix} = \begin{bmatrix} E_{op} e^{j(\omega t - kz - \phi_p)} \\ E_{os} e^{j(\omega t - kz + \phi_s)} \end{bmatrix} \propto \begin{bmatrix} E_{op} e^{j\Delta} \\ E_{os} \end{bmatrix} \quad (2)$$

wherein $E_{op}$ and $E_{os}$ represent the amplitudes of the electric fields $E_p$ and $E_s$ respectively, $j=\sqrt{-1}$, and $\Delta=\phi_p-\phi_s$. The traveling direction of the electric field E is along the z axis. If two polarized electric fields $E_{ip}$ and $E_{is}$ are inputted, two outputted electric fields $E_{rp}$ and $E_{rs}$ can be measured after the two inputted electric fields $E_{ip}$ and $E_{is}$ pass through a sample. Therefore, the related reflection coefficients can be given by:

$$r_p = \frac{E_{rp}}{E_{ip}} = \rho_p e^{j\Delta_p} \quad (3)$$

$$r_s = \frac{E_{rp}}{E_{ip}} = \rho_s e^{j\Delta_s} \quad (4)$$

wherein $\Delta_p$ represents the phase shift of the reflected electric field $E_p$, and $\Delta_s$ represents the phase shift of the reflected electric field $E_s$. Thus, the polarization transfer function F (ellipsomeric function p) of the sample can be defined by:

$$F = \rho = \frac{\frac{E_{rP}}{E_{rs}}}{\frac{E_{ip}}{E_{is}}} = \frac{\frac{E_{rp}}{E_{ip}}}{\frac{E_{rs}}{E_{is}}} = \frac{r_p}{r_s} = \frac{\rho_p e^{j\Delta_p}}{\rho_s e^{j\Delta_s}} = \tan\Psi e^{j\Delta} \quad (5)$$

wherein $$\tan\Psi = \frac{\rho_p}{\rho_s}$$

and $\Delta=\Delta_p-\Delta_s$. The tan $\psi$ and $\Delta$ are called ellipsomeric parameters.

Referring to FIG. 1, a general PMSA type ellipsometer is shown, wherein reference numeral 15 designates a polarizer having a pass axis angle b, 22 designates a phase modulator having m as the azimuth of a fast axis, 30 designates a sample, 42 designates an analyzer having a pass axis angle a, and 45 designates a detector. As shown in FIG. 1, a total of 6 parameters related to the four devices is the pass axis angle coordinate b of the polarizer P designated by a numeral 15, the azimuth angle m of the phase modulator M designated by a numeral 22, phase delay δ of a phase retarder, the ellipsomeric parameters Ψ, Δ and pass axis angle coordinate α of the analyzer A designated by a numeral 42. They can be expressed by Jones' matrixes as follows:

$$P = \begin{bmatrix} \cos^2 b & \sin b \cos b \\ \sin b \cos b & \sin^2 b \end{bmatrix} \quad (6)$$

$$M = \begin{bmatrix} e^{\frac{i\delta}{2}}\cos^2 m + e^{\frac{-i\delta}{2}}\sin^2 m & 2i\sin m\cos m\sin\left(\frac{\delta}{2}\right) \\ 2i\sin m\cos m\sin\left(\frac{\delta}{2}\right) & e^{\frac{-i\delta}{2}}\cos^2 m + e^{\frac{i\delta}{2}}\sin^2 m \end{bmatrix} \quad (7)$$

$$S = \begin{bmatrix} \tan\Psi e^{j\Delta} & 0 \\ 0 & 1 \end{bmatrix} \quad (8)$$

$$A = \begin{bmatrix} \cos^2 a & \sin a \cos a \\ \sin a \cos a & \sin^2 a \end{bmatrix} \quad (9)$$

If the detector 45 has a linear response, a signal I measured after passing through the analyzer 42 can be expressed by:

$$I = G\vec{E}^+ \text{out} \vec{E} \text{out} = G(ASMP\vec{E} \text{ in,})^+ (ASMP\vec{E} \text{ in}) \quad (10)$$

According to "Improvement of phase-modulated ellipsometry" issued on "Review of Scientific Instruents", vol. 60, p.p. 65–77, by Acher, O., E. Bigan, formula (10) can be further expressed as:

$$I(\delta) = G[I + I_s \sin(\delta) + I_c \cos(\delta)] \quad (11)$$

wherein $I_s$ and $I_c$ represents the intensities of the electric fields $E_p$ and $E_s$, respectively.

$$I(\delta) = G\begin{bmatrix} (1-\cos 2\Psi \cos 2a) + \cos 2m \cos 2(m-b)(\cos 2a - \cos 2\Psi) + \\ \sin 2a \cos\Delta \sin 2\Psi \sin 2m \cos 2(m-b) \end{bmatrix} \quad (12)$$

$$I_s = -\sin 2\Psi \sin 2a \sin 2(m-b)\sin \Delta \quad (13)$$

$$I_c = -\sin 2(m-b)[\sin 2m(\cos 2\Psi - \cos 2a) + \sin 2\Psi \cos 2m \cos \Delta] \quad (14)$$

Constant G is determined by the sensitivity of the detector 45, linear circuit amplification ratio and the ellipsomeric parameters. If any one of the parameters P, M, δ and A is modulated by time, then using a lock-in amplifier, the ellipsomeric parameters ψ, Δ and G can be obtained from formula (11). The thickness of the sample can then be estimated.

The phase-shifting ellipsometer having the prior PMSA configuration employs a phase modulator to shift the phase of light to 0, $\pi/2$, and $\pi$ respectively, so as to measure the ellipsomeric parameters.

The only difference between the phase-analysis ellipsometer and the phase-shifting ellipsometer is that the polarizer, phase modulator, analyzer, etc. have different angle parameters. With above mentioned angle parameters, the reflection coefficients $r_p$, $r_s$ of the electric fields $E_p$, Es can be measured directly. Meanwhile, analysis can be performed using methods well-known in prior art phase-analysis ellipsometers.

SUMMARY OF THE INVENTION

In view of the above, the invention is to provide an ellipsometer for measuring the complex refractive index and thin film thickness of a sample, which not only has all complete functions like the conventional ellipsometer, but also is small in volume, can precisely control the angle and direction of an incident light beam with respect to a sample and is easy to use. Moreover, without employing additional and details calibration procedures typically needed for traditional ellipsometers, the ellipsometer disclosed in this invention can be widely applied in semiconductor, optical and chemical industries for measuring the complex refractive index and thin film thickness of the sample.

A first ellipsometer for measuring the complex refractive index and thin film thickness of a sample according to the invention includes a linear polarized light source used to generate a measuring beam for probing the sample; a phase modulator used to control the phase of the measuring beam thereby to generate a sampling beam; a reference analyzer used to generate a reference beam according to part of the sampling beam thereby to adjust the intensity of the sampling beam; a polarization analyzer used to analyze the phase, polarization and intensity of the sampling beam after the sampling beam is reflected by the sample; and a light direction controller used to control the incident angle and direction of the sampling beam with respect to the sample, wherein the sampling beam is reflected by the sample to enter the light direction controller, and thereafter the sampling beam is reflected by the light direction controller and re-reflected by the sample to enter the polarization analyzer along an original optical path, but toward an opposite direction.

A second ellipsometer for measuring the complex refractive index and thin film thickness of a sample according to the invention includes a linear polarized light source used to generate a measuring beam for probing the sample; a phase modulator used to control the phase of the measuring beam thereby to generate a sampling beam; a reference analyzer used to generate a reference beam according to part of the sampling beam to adjust the intensity of the sampling beam; a polarization analyzer used to analyze the phase, polarization and intensity of the sampling beam after the sampling beam is reflected by the sample; and a light direction controller used to control the incident angle and direction of the sampling beam with respect to the sample, wherein the sampling beam is reflected by the sample to enter the light direction controller, and thereafter the sampling beam is reflected by the light direction controller and re-reflected by the sample to enter the polarization analyzer along an original optical path, but toward an opposite direction; and an ellipsomeric parameter calibrator used to replace the sample to allow the sampling beam be perpendicularly incident to the surface of the ellipsomeric parameter calibrator and perpendicularly reflected when the ellipsomeric parameters of the phase modulator, the reference analyzer and the polarization analyzer are calibrated.

A third ellipsometer for measuring the complex refractive index and thin film thickness of a sample through a transparent or translucent medium according to the invention includes a linear polarized light source used to generate a measuring beam for probing the sample; a phase modulator used to control the phase of the measuring beam thereby to generate a sampling beam; a reference analyzer used to generate a reference beam according to part of the sampling beam to adjust the intensity of the sampling beam; a polarization analyzer used to analyze the phase, polarization and intensity of the sampling beam after the sampling beam is reflected by the sample; and a light direction controller used to control the incident angle and direction of the sampling beam with respect to the sample, wherein the sampling beam is reflected by the sample to enter the light direction controller through the medium, and thereafter the sampling beam is reflected by the light direction controller to pass through the medium and re-reflected by the sample to enter the polarization analyzer along an original optical path, but toward an opposite direction A fourth ellipsometer for measuring the complex refractive index and thin film thickness of a sample through a transparent or translucent medium according to the invention includes a linear polarized light source used to generate a measuring beam for probing the sample; a phase modulator used to control the phase of the measuring beam thereby to generate a sampling beam; a reference analyzer used to generate a reference beam according part of the sampling beam to adjust the intensity of the sampling beam; a polarization analyzer used to analyze the phase, polarization and intensity of the sampling beam after the sampling beam is reflected by the sample; a light direction controller used to control the incident angle and direction of the sampling beam with respect to the sample, wherein the sampling beam is reflected by the sample to enter the light direction controller through the medium, and thereafter the sampling beam is reflected by the light direction controller to pass through the medium and re-reflected by the sample to enter the polarization analyzer along an original optical path, but toward an opposite direction; and an ellipsomeric parameter calibrator used to replace the sample to allow the sampling beam be perpendicularly incident to the surface of the ellipsomeric parameter calibrator and perpendicularly reflected when the ellipsomeric parameters of the phase modulator, the reference analyzer, the polarization analyzer and the medium are calibrated.

BRIEF DESCRIPTION OF THE DRAWINGS

The invention will become more fully understood from the detailed description given hereinafter and the accompanying drawings which are given by way of illustration only, and thus do not limit the present invention, and wherein.

DETAILED DESCRIPTION OF THE PREFERRED EMBODIMENTS

Figure 1:
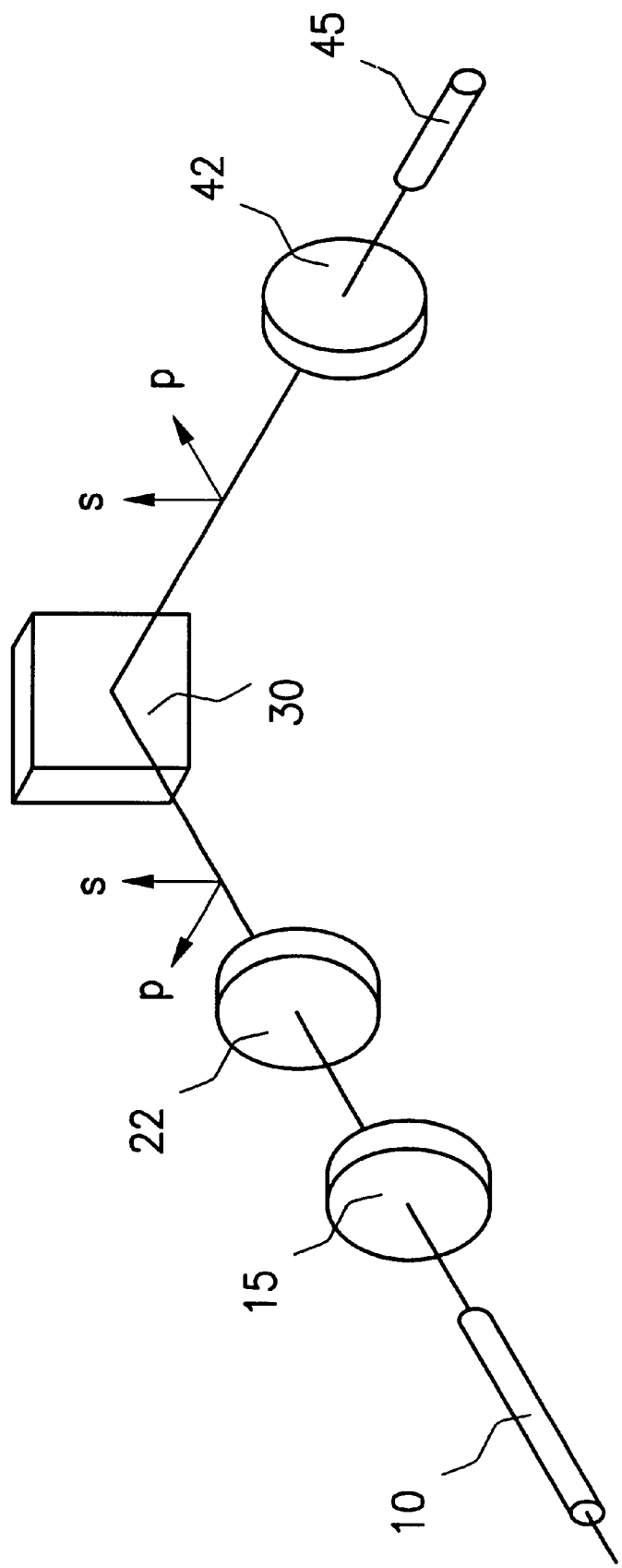
FIG. 1 is a schematic view showing an ellipsometer for measuring the complex refractive index and thin film thickness of a sample according to the prior art.
Figure 2:
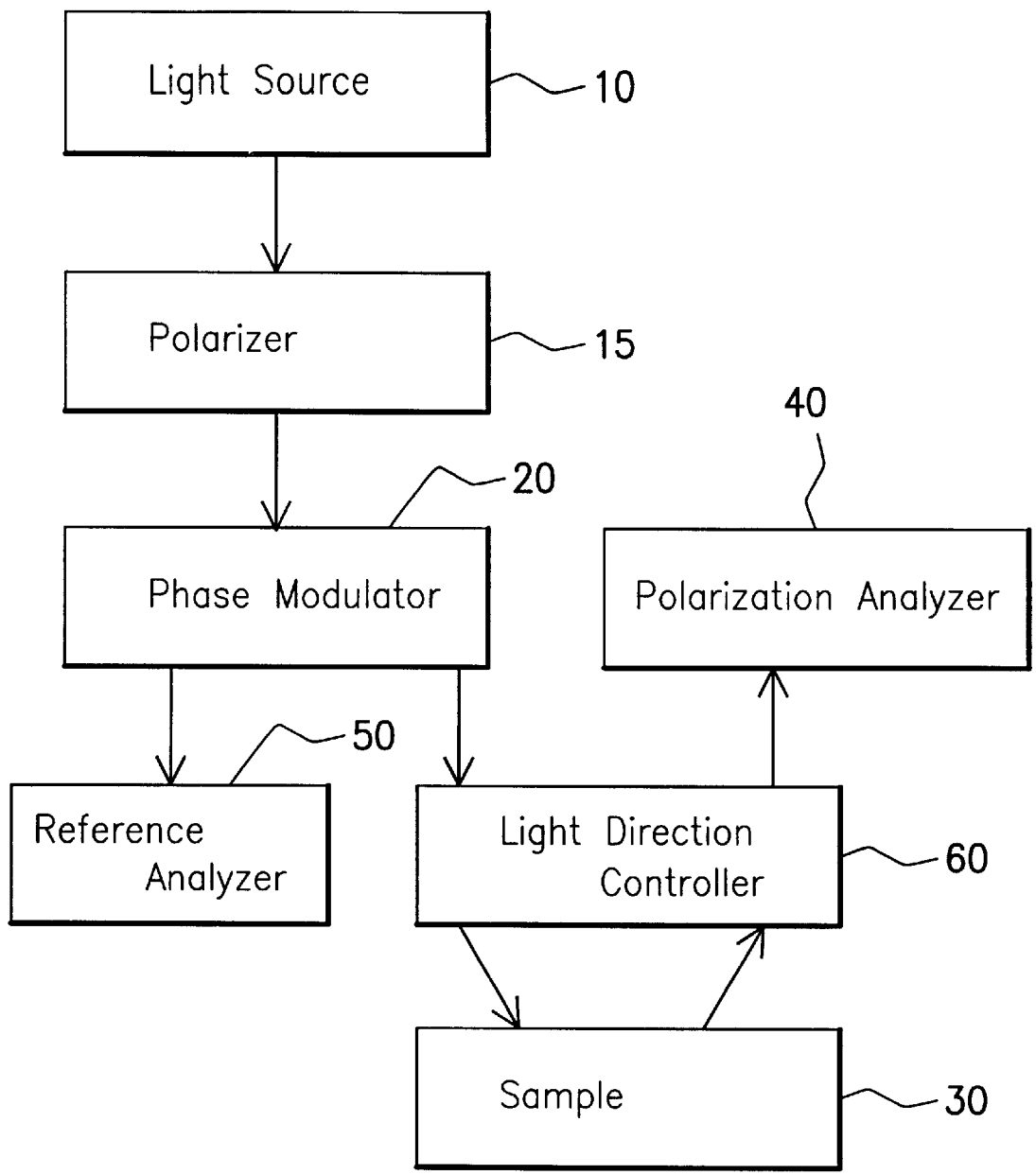
FIG. 2 is a block diagram showing an ellipsometer for measuring the complex refractive index and thin film thickness of a sample according to the present invention.

First, FIG. 2 shows an ellipsometer for measuring the complex refractive index and the thin film thickness of a sample according to the invention. The inventive ellipsometer includes a light source 10, a polarizer 15, a phase modulator 20, a polarization analyzer 40, a reference analyzer 50 and a light direction controller 60. The phase modulator 20 is used to control the phase of a measured beam. The reference analyzer 50 is used to adjust the intensity of the measured beam. The light direction controller 60 is used to control the incident angle and direction of the measured beam with respect to a sample 30 so as to allow the measured beam to be re-reflected from the sample 30 back to the light direction controller 60 along an original optical path, then to the polarization analyzer 40.

The polarizer 15 can be any device which is able to polarize the measured beam. The phase modulator 20 can be liquid crystal plus a feed-back control mechanism. The light direction controller 60 can consist of a penta prism, a concave parabolic mirror, a concave spherical mirror and a feed-back control two-dimension (x, y) stage. Alternatively, the light direction controller 60 may consist of a penta prism, a quasi-concave parabolic mirror, a quasi-concave spherical mirror and a feed-back control two-dimension (x, y) stage. The polarization analyzer 40 can be an analyzing device and a detector plus a charge couple device (CCD) for feed-back and controlling the position of the sample 30.

Jones' vector and Jones' matrix of each above-stated device which the measured beam passes through can be expressed by: for an incident beam:

$$E_i = \begin{bmatrix} E_p \\ E_s \end{bmatrix} \quad (15)$$

for the polarizer 15:

$$P = \text{Polarizer} = \begin{bmatrix} \cos^2 b & \sin b \cos b \\ \sin b \cos b & \sin^2 b \end{bmatrix} \quad (16)$$

for the sample 30:

$$S = \text{Sample} = \begin{bmatrix} |R_p|e^{j\delta_p} & 0 \\ 0 & |R_s|e^{j\delta_s} \end{bmatrix} =$$

$$|R_s|e^{j\delta_s} \begin{bmatrix} \tan\Psi e^{j\Delta} & 0 \\ 0 & 1 \end{bmatrix} = \begin{bmatrix} \tan\Psi e^{j\Delta} & 0 \\ 0 & 1 \end{bmatrix} \quad (17)$$

for the phase modulator 20:

$$M = \text{Retarder} = \begin{bmatrix} e^{\frac{j\delta}{2}}\cos^2 m + e^{\frac{-j\delta}{2}}\sin^2 m & 2j\sin m \cos m \sin\left(\frac{\delta}{2}\right) \\ 2j\sin m \cos m \sin\left(\frac{\delta}{2}\right) & e^{\frac{-j\delta}{2}}\cos^2 m + e^{\frac{j\delta}{2}}\sin^2 m \end{bmatrix} \quad (18)$$

for the analyzer 40:

$$A = \text{Analyzer} = \begin{bmatrix} \cos^2 a & \sin a \cos a \\ \sin a \cos a & \sin^2 a \end{bmatrix} \quad (19)$$

The configuration of the ellipsometer follows the general PMSA configuration, and therefore, $$E_r = ASMPE_i \quad (20)$$

If b=0°, m=45° and a=45°, the intensity I of the beam can be obtained by:

$$I = GE_r^+ E_r = G(ASMPE_i)^+(ASMPE_i) = G(I_o + I_s \sin\delta + I_c \cos\delta) \quad (21)$$

wherein $$I_o = 1 \quad (22)$$

$$I_s = -\sin 2\Psi \sin\Delta \quad (23)$$

$$I_c = -\cos 2\Psi \quad (24)$$

$$I(\delta) = G[1 - (\sin 2\Psi \sin\Delta)\sin\delta - \cos 2\Psi \cos\delta] \quad (25)$$

To make the invention more understandable, four preferred embodiments will be described hereinafter.

FIRST EMBODIMENT

Figure 3:
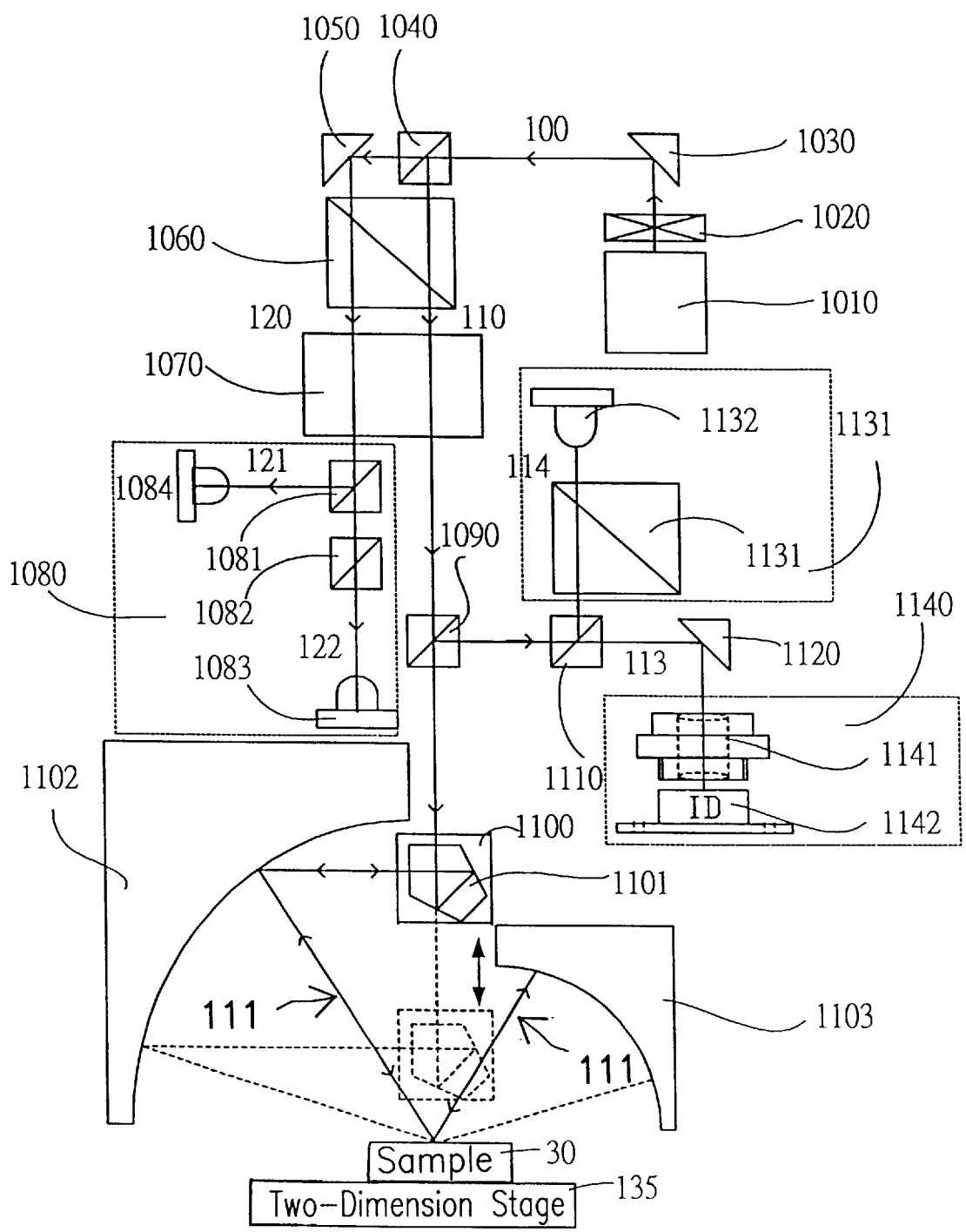
FIG. 3 is a layout of an ellipsometer according to a first preferred embodiment.

Referring to FIG. 3, a layout of an ellipsometer according to a first preferred embodiment is shown. A polarizer 1060 is a linear polarizing device. A phase modulator 1070 consists of a liquid crystal modulator plus a feed-back control mechanism (not shown). The light direction controller 60 consists of a penta prism 1101, a concave paraboloidal mirror 1102, a concave spherical mirror 1103, a one-dimension shift stage 1100 for carrying the penta prism 1101 and a two-dimension (x, y) stage 135 for carrying the sample 30 and having a feed-back function. The polarization analyzer 40 includes an analyzer 1131, a detector 1132 and an imaging device (ID) 1142 such as a coupled device for feed-back and controlling the position of the sample 30. More detailed description will be explained hereinafter.

As shown in FIG. 3, a light source 1010 emits a beam 100. The beam 100 is properly adjusted to a desired intensity by an attenuator 1020 and then divided into a sampling beam 110 and a reference beam 120 after entering the non-polarizing beam splitter 1040 after reflected by a reflective mirror 1030. The reference beam 120 and the sampling beam 110 are parallel to each other and pass through the polarizer 1060 and the phase modulator 1070 together in sequence after the reference beam 120 is reflected by a reflective mirror 1050. The reference beam 120 is divided into two beams 121, 122 after passing through a non-polarizing beam splitter 1081. The beam enters a detector 1084 while the beam 122 is incident to a detector 1083 through an analyzer 1082. The sampling beam 110 enters the light direction controller 60 (as shown in FIG. 2) through a non-polarizing beam splitter 1090. The light direction controller 60 is used to control the angle and direction of the sampling beam 110 incident to the sample 30 thereby to make the sampling beam be reflected from the sample 30 back to the light direction controller 60 along an original optical path, and then enter the polarization analyzer 40. That is, the sampling beam 110 is refracted by a penta prism 1101, reflected by a concave paraboloidal mirror 1102 into the sample 30, and then reflected by the sample 30 into a concave spherical mirror 1103 along an optical path 111. Thereafter, the sampling beam 110 is further reflected by the concave parabolic mirror 1103, the sample 30 and the concave paraboloidal mirror 1102 and refracted by the penta prism 1101 in sequence along the original optical path 111, but having an opposite direction. Then, the sampling beam coming from the penta prism 1101 is refracted by the non-polarizing beam splitter 1090 into another non-polarizing beam splitter 1110. The non-polarizing beam splitter 1110 further splits the sampling beam 110 into two beam 113, 114. The beam 113 is reflected by a reflective mirror 1120 into an image device 1142 such as a charge coupled device. The beam 114 is incident to a detector 1132 through an analyzer 1131.

In addition to the Jones' vectors and Jones' matrixes for the above-stated $E_i$, $E_r$, polarizer 15, sample 30 and analyzer 40, Jones' vectors and Jones matrixes for other devices along which the sampling beam 110 enters the polarization analyzer 40 from the light direction controller 60 can be expressed by: for the prism:

$$X = \begin{bmatrix} \tan\Psi_x e^{j\Delta_x} & 0 \\ 0 & 1 \end{bmatrix} \quad (26)$$

for the parabolic mirror:

$$Y = \begin{bmatrix} \tan\Psi_y e^{j\Delta_x} & 0 \\ 0 & 1 \end{bmatrix} \quad (27)$$

for the convex spherical mirror:

$$Z = \begin{bmatrix} -1 & 0 \\ 0 & 1 \end{bmatrix} \quad (28)$$

for the concave spherical mirror:

$$W = \begin{bmatrix} -1 & 0 \\ 0 & 1 \end{bmatrix} \quad (29)$$

if b=0°, m=45° and a=45°, the configuration of the ellipsometer, PMXYSWSYXA, can be expressed by:

$$E_r = AXYSWSYXMPE_i = AS_0MPE_i \quad (30)$$

wherein $$S_0 = XYSWSYX = \begin{bmatrix} -\tan^2\Psi_x\tan^2\Psi e^{j(2\Delta_x+2\Delta_y+2\Delta)} & 0 \\ 0 & 1 \end{bmatrix} \quad (31)$$

$$= \begin{bmatrix} \tan^2\Psi_x\tan^2\Psi_y\tan^2\Psi e^{j(2\Delta_x+2\Delta_y+2\Delta+\pi)} & 0 \\ 0 & 1 \end{bmatrix} \begin{bmatrix} \tan\Psi_0 e^{j\Delta_0} & 0 \\ 0 & 1 \end{bmatrix}$$

$$\tan\Psi_0 = \tan^2\Psi_x \tan^2\Psi_y \tan^2\Psi$$

$$\Delta_0 = 2\Delta_x + 2\Delta_y + 2\Delta + \pi$$

$$I = GE_r^+ E_r = G(AS_0MPE_i)^+(AS_0MPE_i) = G[1-(\sin 2\Psi_0 \sin \Delta_0) \sin \delta - \cos 2\Psi_0 \cos \delta] \quad (32)$$

The above-stated transfer function of the ellipsometer can be measured using the convex spherical mirror 1104, and therefor, $\Psi_o$ and $\Delta_o$ can be obtained using the above-stated transfer function.

Figure 4:
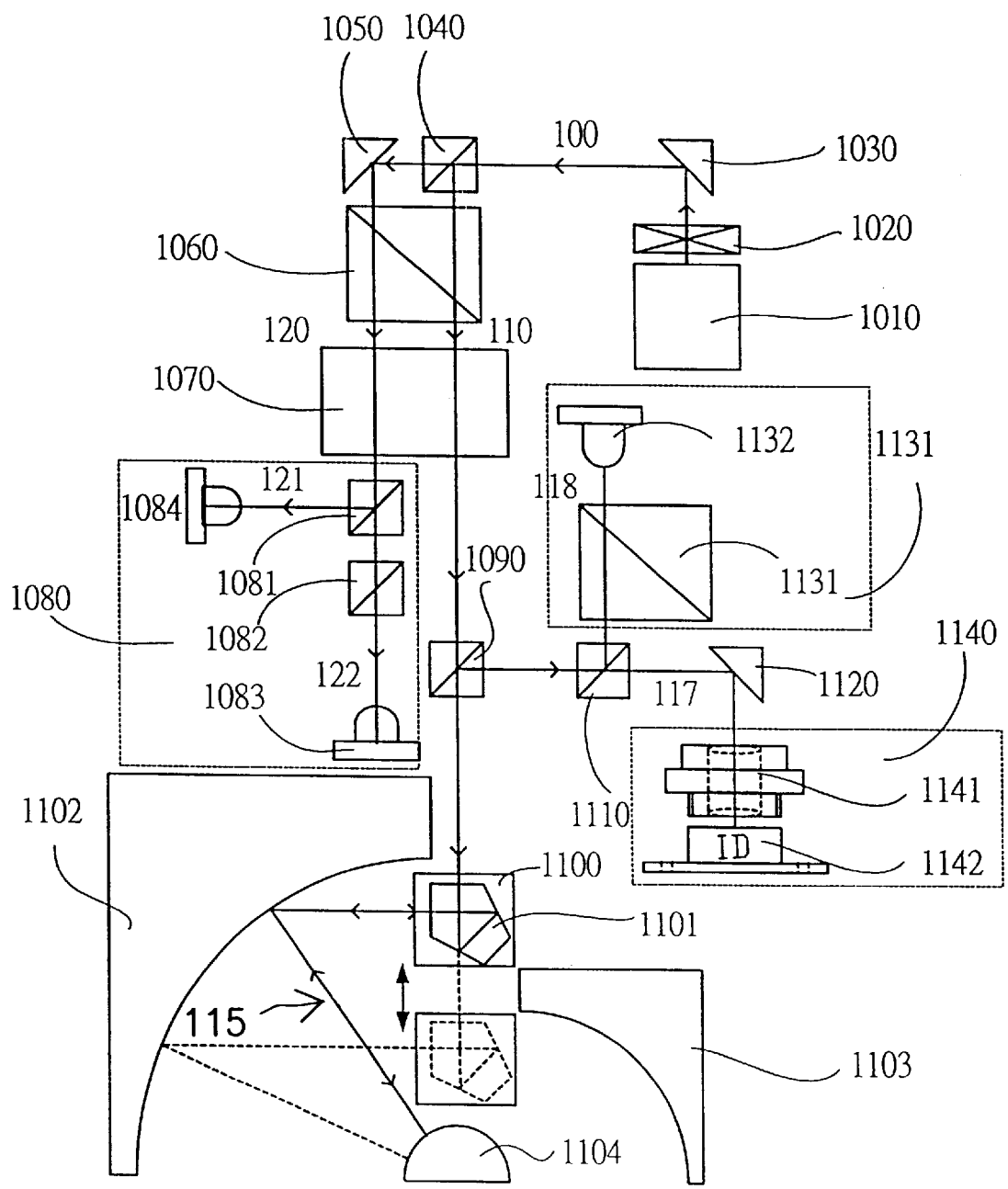
FIG. 4 is a schematic view showing the measurement of the transfer function of the ellipsometer of FIG. 3 using a convex spherical mirror.

Referring now to FIG. 4, using a convex spherical mirror to measure the transfer function of the ellipsometer of FIG. 3 is shown. In FIG. 4, the sampling beam 110 is refracted by the penta prism 1101 and then reflected by the concave paraboloidal mirror 1102 and the convex spherical mirror 1104 along an optical path 115. Thereafter, the sampling beam 110 is further reflected by the convex spherical mirror 1104 and the concave paraboloidal mirror 1102 in sequence and then refracted by the penta prism 1101 along the original optical path 115, but toward an opposite direction. After being refracted by the penta prism 1101, the sampling beam 110 is divided by the non-polarizing beam splitter 1110 into two beams 117, 118. The beam 117 is reflected by the reflective mirror 1120 to enter an imaging device 1142 such as charge coupled device while the beam 118 is incident to the detector 1132 through an analyzer 1131. A configuration PMXYZYXA formed as the optical path passes through each device can be expressed by:

$$E_r = AXYZYXMPE_i = AS_1MPE_i \quad (33)$$

wherein $$S_1 = XYZYX \quad (34)$$

$$= \begin{bmatrix} -\tan^2\Psi_x\tan^2\Psi_y e^{j(2\Delta_x+2\Delta_y)} & 0 \\ 0 & 1 \end{bmatrix}$$

$$= \begin{bmatrix} -\tan^2\Psi_x\tan^2\Psi_y e^{j(2\Delta_x+2\Delta_y+\pi)} & 0 \\ 0 & 1 \end{bmatrix}$$

$$= \begin{bmatrix} \tan\Psi_1 e^{j\Delta_1} & 0 \\ 0 & 1 \end{bmatrix}$$

$$\tan\Psi_1 = \tan^2\Psi_x \tan^2\Psi_y$$

$$\Delta_1 = 2\Delta_x + 2\Delta_y + \pi$$

$$I = GE_r^+ E_r = G(AS_1MPE_i)^+(AS_1MPE_i) = G[1-(\sin 2\Psi_1 \sin \Delta_1) \sin \delta - \cos 2\Psi_1 \cos \delta] \quad (35)$$

Therefore, $\Psi_1$, and $\Delta_1$ can be obtained so as to calculate the transfer function $\tan^2\Psi_x \tan^2\Psi_y e^{j(2\Delta_x+2\Delta_y+\pi)}$. According to the above steps, the unknown ellipsomeric parameters $\Psi$ and $\Delta$ of the sample 30 can be obtained. As a result, the thickness and the complex refraction index of the sample can also be calculated. It is should be noted that the convex spherical mirror 1104 is mainly used to allow the sampling beam 110 to be perpendicularly incident to and perpendicularly reflected from the convex spherical mirror 1104. Since the convex spherical mirror 1104 is used only when the calibration for the transfer function of the inventive ellipsometer is performed, it can be replaced with a mirror as long as the sampling beam 110 can be perpendicularly incident and reflected.

SECOND EMBODIMENT

Figure 5:
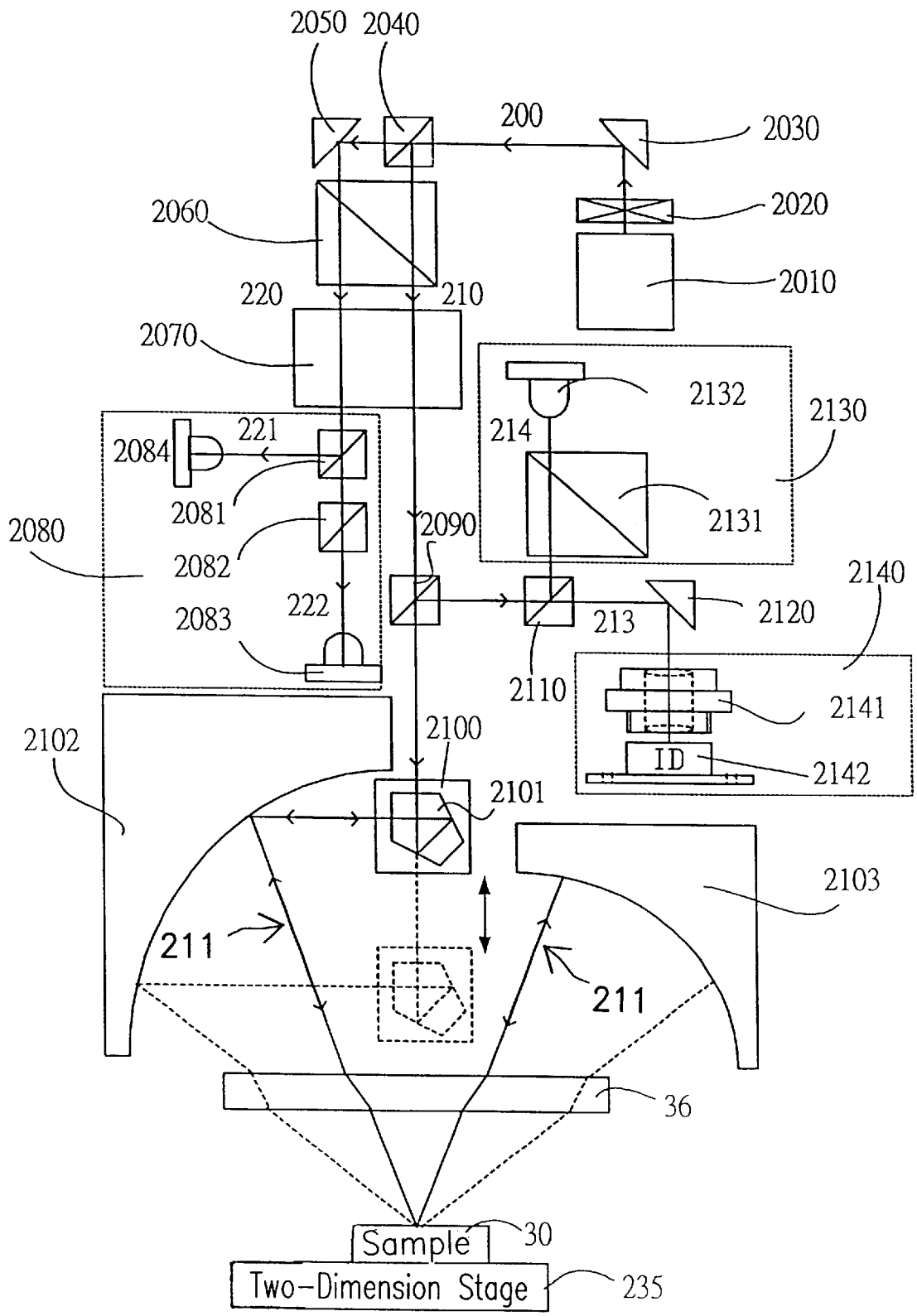
FIG. 5 is a layout of an ellipsometer according to a second preferred embodiment.

Referring to FIG. 5, a layout of an ellipsometer according to a second preferred embodiment is shown. The features of the ellipsometer of the second preferred embodiment are that a sampling beam 110 can be incident to a specific measurement point on the surface of a sample 30 through a transparent or translucent medium 36, and the incident angle of the sampling beam 110 with respect to the sample 30 can be changed without changing the position of the specific measurement point. With the ellipsometer according to the second embodiment, the sample 30 is placed under the transparent or translucent medium 36 directly with a larger distance therebetween. Furthermore, not only the ellipsomeric parameter of the sample 30 can be obtained thereby to calculate the thickness and complex refractive index of the sample 30, but also the ellipsomeric parameter of the transparent or translucent medium 36 can be obtained thereby to calculate the thickness and complex refractive index of the transparent or translucent medium 36. As to the structure of the ellipsometer of the second preferred embodiment, a polarizer 2060 is a linear polarizing device. A phase modulator 2070 consists of a liquid crystal modulator plus a feed-back control mechanism (not shown). A light direction controller 60 (shown in FIG. 2) can control the incident angle and direction of an incident beam with respect to the sample 30 and allow the incident beam to be reflected from the sample 30 back to the light direction controller 60 along an original optical path and then enter a polarization analyzer 40 (shown in FIG. 2). The light direction controller 60 consists of a penta prism 2101, a concave paraboloidal mirror 2102, a concave spherical mirror 2103, a one-dimension shift stage 2100 for carry the penta prism 2101 and a two-dimension (x, y) stage 235 having a feed-back function for carrying the sample 30. The polarization analyzer 40 includes an analyzer 2131, a detector 2132 and an image device (ID) 2142 such as a charge coupled device for feeding back and controlling the position of the sample 30. More detailed description will be explained hereinafter.

As shown in FIG. 5, a light source 2010 emits a beam 200. The beam 200 is properly adjusted to a desired intensity by an attenuator 2020 and then divided into a sampling beam 210 and a reference beam 220 after entering the non-polarizing beam splitter 2040 after reflected by a reflective mirror 2030. The reference beam 220 and the sampling beam 210 are parallel to each other and pass through the polarizer 2060 and the phase modulator 2070 together in sequence after the reference beam 220 is reflected by a reflective mirror 2050. The reference beam 220 is divided into two beams 221, 222 after passing through a non-polarizing beam splitter 2081. The beam 221 enters a detector 2084 while the beam 222 is incident to a detector 2083 through an analyzer 2082. As to the sampling beam 210, it enters the light direction controller 60 (shown in FIG. 2) through a non-polarizing beam splitter 2090. The light direction controller 60 is used to control the incident angle and direction of the sampling beam 210 with respect to the sample 30 thereby to make the sampling beam 210 pass through the transparent or translucent medium 36 and then be reflected from the sample 30 back to the light direction controller 60 along an original optical path, and then enter the polarization analyzer 40. That is, the sampling beam 210 is refracted by a penta prism 2101, reflected by a concave quasi-paraboloidal mirror 2102 to pass through the transparent or translucent medium 36, and then reflected by the sample 30 to pass through the transparent or translucent medium 36 to reach a concave qusai-spherical mirror 2103 along an optical path 211. Thereafter, the sampling beam 210 is reflected by the concave quasi-paraboloidal mirror 2103 to pass through the transparent or translucent medium 36, reflected by the sample 30 to pass through the transparent or translucent medium 36 again, further reflected by the concave quasi-paraboloidal mirror 2102 and then refracted by the penta prism 2101 along the original optical path 211, but toward an opposite direction. It should be noted that the quasi-paraboloidal mirror 2102 is designed by using a paraboloidal as the starting point and then modified to pre-compensate the aberration caused by the transparent or translucent medium 36 so as to make sure the measurement point identical in space when one-dimensional shift stage 2100 is in different positions. Similarly, the quasi-spherical mirror 2103 is designed by using a spherical mirror as a starting point and then modified to pre-compensate the aberration caused by the transparent or translucent medium 36. Then, the sampling beam 211 coming from the penta prism 2101 is refracted by the non-polarizing beam splitter 2090 to enter another non-polarizing beam splitter 2110. The non-polarizing beam splitter 2110 further splits the sampling beam 210 into two beams 213 and 214. The beam 213 is reflected by a reflective mirror 2120 to enter an image device 2142 such as a charge coupled device while the beam 214 is incident to a detector 2132 through an analyzer 2131.

If b=0°, m=45° and a=45°, the configuration of the ellipsometer according to the second preferred embodiment, PMXYSWSYXA, can be expressed by:

$$E_r = AXYSWSYXMPE_r = AS_0 MPEP_r \quad (36)$$

wherein $$S_0 = XYSWSYX \quad (37)$$

$$= \begin{bmatrix} -\tan^2\Psi_x \tan^2\Psi_y \tan^2\Psi e^{j(2\Delta_x + 2\Delta_y + 2\Delta)} & 0 \\ 0 & 1 \end{bmatrix}$$

$$= \begin{bmatrix} \tan^2\Psi_x \tan^2\Psi_y \tan^2\Psi e^{j(2\Delta_x + 2\Delta_y + 2\Delta + \pi)} & 0 \\ 0 & 1 \end{bmatrix}$$

$$= \begin{bmatrix} \tan\Psi_0 e^{j\Delta_0} & 0 \\ 0 & 1 \end{bmatrix}$$

$$\tan\Psi_1 = \tan^2\Psi_x \tan^2\Psi_y$$

$$\Delta_0 = 2\Delta_x + 2\Delta_y + 2\Delta + \pi$$

$$I = GE_r^+ E_r = G(AS_0 MPE_i)^+(AS_0 MPE_i) = G[1-(\sin 2\Psi_0 \sin \Delta_0) \sin \delta - \cos 2\Psi_0 \cos \delta] \quad (38)$$

The above-stated transfer function of the ellipsometer can be measured using a convex quasi-spherical mirror, and therefore, $\psi_o$ and $\Delta_o$ can be calculated according to the obtained transfer function. More detailed description will be described in the following.

Figure 6:
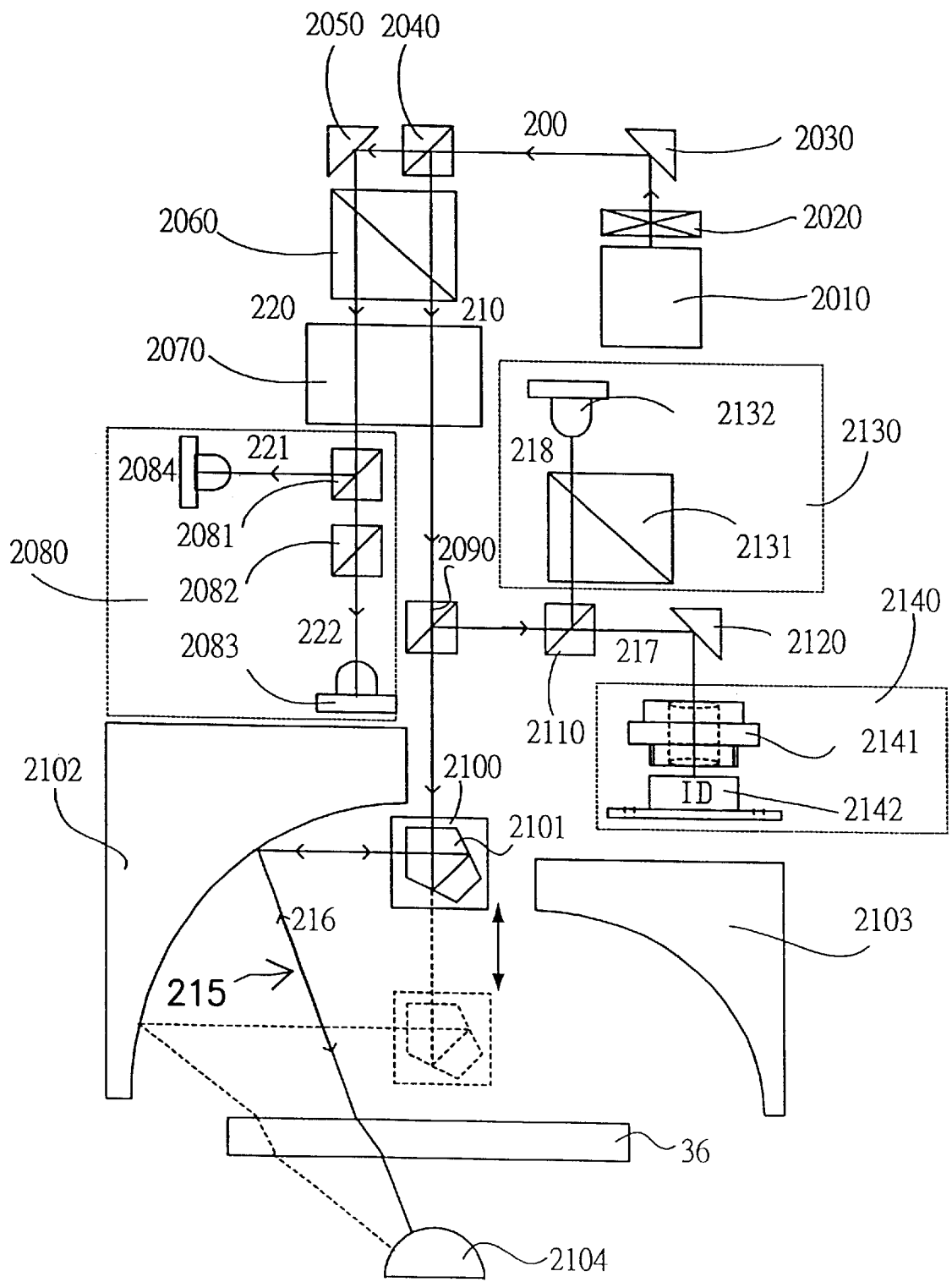
FIG. 6 is a schematic view showing the measurement of the transfer function of the ellipsometer of FIG. 5 using a convex spherical mirror.

Referring now to FIG. 6, using a convex quasi-spherical mirror to measure the transfer function of the ellipsometer of FIG. 5 is shown. In FIG. 6, the sampling beam 210 is refracted by the penta prism 2101, reflected by the concave quasi-paraboloidal mirror 2102 to pass through the transparent or translucent medium 36, and then reflected by the convex quasi-spherical mirror 2104 along an optical path 215. Thereafter, the sampling beam 210 is further reflected by the convex quasi-spherical mirror 2104 to pass through the transparent or translucent medium 36, reflected by the concave quasi-paraboloidal mirror 2102 and then refracted by the penta prism 2101 along the optical path 215, but toward an opposite direction. After being refracted by the penta prism 2101, the sampling beam 210 is divided by the non-polarizing beam splitter 2110 into two beams 217 and 218. The beam 217 is reflected by the reflective mirror 2120 to enter an imaging device 2142 such as a charge coupled device 2142 while the beam 218 is incident to the detector 2132 through the analyzer 2131. A configuration PMXYZYXA formed when the optical path passes through each device can be expressed by:

$$E_r = AXYZYXMPE_i = AS_i MPE_i \quad (39)$$

wherein $$S_0 = XYZYX \quad (40)$$

$$= \begin{bmatrix} -\tan^2\Psi_x \tan^2\Psi_y e^{j(2\Delta_x + 2\Delta_y)} & 0 \\ 0 & 1 \end{bmatrix}$$

$$= \begin{bmatrix} -\tan^2\Psi_x \tan^2\Psi_y e^{j(2\Delta_x + 2\Delta_y + \pi)} & 0 \\ 0 & 1 \end{bmatrix}$$

-continued $$= \begin{bmatrix} \tan\Psi_1 e^{j\Delta_1} & 0 \\ 0 & 1 \end{bmatrix}$$

$$\tan\Psi_1 = \tan^2\Psi_x \tan^2\Psi_y$$

$$\Delta_I = 2\Delta_x + 2\Delta_y + \pi$$

$$I = GE_r^+ E_r = G(AS_I MPE_i)^+(AS_I MPE_i) = G[1-(\sin 2\psi_I \sin \Delta_I)\sin \delta - \cos 2\psi_I \cos \delta] \quad (41)$$

Accordingly, $\psi_I$, and $\Delta_I$, can be obtained so as to calculate the transfer function $\tan^2\psi_x \tan^2\psi_y e^{j(2\Delta_x + 2\Delta_y + \pi)}$. According to the above steps, the ellipsomeric parameters $\psi$ and $\Delta$ of the sample 30 can be obtained. Moreover, the thickness and the complex refraction index of the sample can also be calculated. It is should be noted that the convex quasi-spherical mirror 2104 is mainly used to allow the sampling beam 210 to be perpendicularly incident to and perpendicularly reflected from the convex quasi-spherical mirror 2104. Since the convex spherical mirror 2104 is used only when the calibration for the transfer function of the inventive ellipsometer is performed, it can be replaced with a mirror as long as the sampling beam 210 can be perpendicularly incident and reflected.

As described above, an ellipsometer of the invention not only has all complete functions like the conventional ellipsometer, but also has advantages such as possesses small volume, can precisely control the angle and direction of an incident beam with respect to a sample, and is easy to use. Without resorting to additional and tedious precise calibration, the ellipsometer according to the invention can be widely applied in semiconductor, optical and chemical industries for measuring the complex refractive index and thin film thickness of a sample.

THIRD EMBODIMENT

This third preferred embodiment can be easily desired by using the first embodiment as was disclosed in FIG. 3 and FIG. 4. By first replacing the concave paraboloidal mirror 1102 shown in FIG. 3 and FIG. 4 with a concave parabolic cylindrical mirror, and then replacing the concave spherical mirror 1103 shown in FIG. 3 and FIG. 4 with a concave cylindrical mirror, the measurement area on the sample 30 will be changed from a point to a line. If the photodetector 1132 is also converted to a photodetector array, the third embodiment can be used to probe several measurement points simultaneously.

FOURTH EMBODIMENT

This third preferred embodiment can be easily desired by using the first embodiment as was disclosed in FIG. 5 and FIG. 6. By first replacing the concave quasi-paraboloidal mirror 1102 shown in FIG. 5 and FIG. 6 with a concave quasi-parabolic cylindrical mirror, and then replacing the concave quasi-spherical mirror 1103 shown in FIG. 5 and FIG. 6 with a concave quasi-cylindrical mirror, the measurement area on the sample 30 will be changed from a point to a line. If the photodetector 1132 is also converted to a photodetector array, the third embodiment can be used to probe several measurement points simultaneously.

While the invention has been described by way of example and in terms of the preferred embodiment, it is to be understood that the invention is not limited to the disclosed embodiments. On the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. An ellipsometer for measuring the complex refractive index and thin film thickness of a sample, comprising:
   a linear polarized light source used to generate a measuring beam for probing the sample;
   a phase modulator used to control the phase of the measuring beam thereby to generate a sampling beam;
   a reference analyzer used to generate a reference beam according to part of the sampling beam thereby to adjust the intensity of the sampling beam;
   a polarization analyzer used to analyze the phase, polarization and intensity of the sampling beam after the sampling beam is reflected by the sample; and
   a light direction controller used to control the incident angle and direction of the sampling beam with respect to the sample, wherein the sampling beam is reflected by the sample to enter the light direction controller, and thereafter the sampling beam is reflected by the light direction controller and reflected by the sample to enter the polarization analyzer along an original optical path, but toward an opposite direction, wherein the light direction controller comprises:
      a prism used to refract the sampling beam thereby to turn the sampling beam by 90°;
      a concave paraboloidal mirror used to reflect the sampling beam coming from the prism to enter the sample, wherein the incident angle of the sampling beam with respect to the measurement point of the sample can be changed when the prism moves up and down;
      a concave spherical mirror used to perpendicularly reflect the sampling beam coming from the sample back to the sample; and
      a feed-back control two-dimension stage used to determine the measurement point of the sample.

2. The ellipsometer as defined in claim 1, wherein the linear polarized light source is a laser light source which can emit a linear polarized light.

3. The ellipsometer as defined in claim 1, wherein the linear polarized light source comprises a non-coherent light source and a linear polarizing device.

4. The ellipsometer as defined in claim 1, wherein the linear polarized light source comprises a laser light source and a linear polarizing device.

5. The ellipsometer as defined in claim 1, wherein the phase modulator is a feed-back control system with liquid crystal therein.

6. The ellipsometer as defined in claim 1, wherein the reference analyzer comprises a non-polarizing beam splitter and a detector.

7. The ellipsometer as defined in claim 1, wherein the polarization analyzer comprises a polarizing beam splitter and a detector.

8. An ellipsometer for measuring the complex refractive index and thin film thickness of a sample, comprising:
   a linear polarized light source used to generate a measuring beam for probing the sample;
   a phase modulator used to control the phase of the measuring beam thereby to generate a sampling beam;
   a reference analyzer used to generate a reference beam according to part of the sampling beam thereby to adjust the intensity of the sampling beam;

a polarization analyzer used to analyze the phase, polarization and intensity of the sampling beam after the sampling beam is reflected by the sample; and a light direction controller used to control the incident angle and direction of the sampling beam with respect to the sample, wherein the sampling beam is reflected by the sample to enter the light direction controller, and thereafter the sampling beam is reflected by the light direction controller and re-reflected by the sample to enter the polarization analyzer along an original optical path, but toward an opposite direction, wherein the light direction controller comprises:

a prism used to refract the sampling beam thereby to turn the sampling beam by 90°;

a concave parabolic cylindrical mirror used to reflect the sampling beam coming from the prism to enter the sample, wherein the incident angle of the sampling beam with respect to the measured area of the sample can be changed when the prism moves up and down;

a concave cylindrical mirror used to perpendicularly reflect the sampling beam coming from the sample back to the sample; and a feed-back control two-dimension stage for determining the measurement area of the sample.

9. The ellipsometer as defined in claim 8, wherein the linear polarized light source is a laser light source which can emit a linear polarized light.

10. The ellipsometer as defined in claim 8, wherein the linear polarized light source comprises a non-coherent light source and a linear polarizing device.

11. The ellipsometer as defined in claim 8, wherein the linear polarized light source comprises a laser light source and a linear polarizing device.

12. The ellipsometer as defined in claim 8, wherein the phase modulator is a feed-back control system with liquid crystal therein.

13. The ellipsometer as defined in claim 8, wherein the reference analyzer comprises a non-polarizing beam splitter and a detector.

14. The ellipsometer as defined in claim 8, wherein the polarization analyzer comprises a polarizing beam splitter and a detector.

15. An ellipsometer for measuring the complex refractive index and thin film thickness of a sample, comprising:

a linear polarized light source used to generate a measuring beam for detecting the sample;

a phase modulator used to control the phase of the measuring beam thereby to generate a sampling beam;

a reference analyzer used to generate a reference beam according to part of the sampling beam to adjust the intensity of the sampling beam;

a polarization analyzer used to analyze the phase, polarization and intensity of the sampling beam after the sampling beam is reflected by the sample; and a light direction controller used to control the incident angle and direction of the sampling beam with respect to the sample, wherein the sampling beam is reflected by the sample to enter the light direction controller, and thereafter the sampling beam is reflected by the light direction controller and re-reflected by the sample to enter the polarization analyzer along an original optical path, but toward an opposite direction; and an ellipsomeric parameter calibrator used to replace the sample to allow the sampling beam be perpendicularly incident to the surface of the ellipsomeric parameter calibrator and perpendicularly reflected when the ellipsomeric parameters of the phase modulator, the reference analyzer and the polarization analyzer are calibrated.

16. The ellipsometer as defined in claim 15, wherein the linear polarized light source is a laser light source which can emit a linear polarized light.

17. The ellipsometer as defined in claim 15, wherein the linear polarized light source comprises of a non-coherent light source and a linear polarizing device.

18. The ellipsometer as defined in claim 15, wherein the linear polarized light source comprises a laser light source and a linear polarizing device.

19. The ellipsometer as defined in claim 15, wherein the phase modulator is a feed-back control system with liquid crystal therein.

20. The ellipsometer as defined in claim 15, wherein the reference analyzer comprises a non-polarizing beam splitter and a detector.

21. The ellipsometer as defined in claim 15, wherein the polarization analyzer comprises a polarizing beam splitter and a detector.

22. The ellipsometer as defined in claim 15, wherein the light direction controller comprises:

a prism used to refract the sampling beam thereby to turn the sampling beam by 90°;

a concave paraboloidal mirror used to reflect the sampling beam coming from the prism to enter the sample, wherein the incident angle of the sampling beam with respect to the measurement point of the sample can be changed when the prism moves up and down;

a concave spherical mirror used to perpendicularly reflect the sampling beam coming from the sample back to the sample; and a feed-back control two-dimension stage for determining the measurement point of the sample.

23. The ellipsometer as defined in claim 15, wherein the light direction controller comprises:

a prism used to refract the sampling beam thereby to turn the sampling beam by 90°;

a concave parabolic cylindrical mirror used to reflect the sampling beam coming from the prism to enter the sample, wherein the incident angle of the sampling beam with respect to the measured area of the sample can be changed when the prism moves up and down;

a concave cylindrical mirror used to perpendicularly reflect the sampling beam coming from the sample back to the sample; and a feed-back control two-dimension stage for determining the measurement area of the sample.

24. The ellipsometer as defined in claim 15, wherein the ellipsomeric parameter calibrator uses a convex spherical mirror to replace the sample thereby to make the sampling beam be perpendicularly incident to the convex spherical mirror when calibration is performed.

25. The ellipsometer as defined in claim 15, wherein the ellipsomeric parameter calibrator uses a planar mirror that is gradually adjusted according to the incident angle of the sampling beam to ensure that the incident beam is perpendicularly incident to the planar mirror when calibration is performed.

26. The ellipsometer as defined in claim 15, wherein the ellipsomeric parameter calibrator uses a standard sample with known ellipsomeric parameters for calibration.

27. An ellipsometer for measuring the complex refractive index and thin film thickness of a sample through a transparent or translucent medium, comprising:

a linear polarized light source used to generate a measuring beam for detecting the sample;

a phase modulator used to control the phase of the measuring beam thereby to generate a sampling beam;

a reference analyzer used to generate a reference beam according part of the sampling beam to adjust the intensity of the sampling beam;

a polarization analyzer used to analyze the phase, polarization and intensity of the sampling beam after the sampling beam is reflected by the sample; and a light direction controller used to control the incident angle and direction of the sampling beam with respect to the sample, wherein the sampling beam is reflected by the sample to enter the light direction controller through the medium, and thereafter the sampling beam is reflected by the light direction controller to pass through the medium and re-reflected by the sample to enter the polarization analyzer along an original optical path, but toward an opposite direction, wherein the light direction controller comprises:

a prism used to refract the sampling beam thereby to turn the sampling beam by 90°;

a concave quasi-paraboloidal mirror used to reflect the sampling beam coming from the prism to enter the sample through the medium, wherein the incident angle of the sampling beam with respect to the measurement point of the sample can be changed when the prism moves up and down;

a concave quasi-spherical mirror used to perpendicularly reflect the sampling beam coming from the sample back to the sample through the medium; and a feed-back control two-dimension stage used to determine the measurement point of the sample.

28. The ellipsometer as defined in claim 27, wherein the linear polarized light source is a laser light source which can emit a linear polarized light.

29. The ellipsometer as defined in claim 27, wherein the linear polarized light source comprises a non-coherent light source and a linear polarizing device.

30. The ellipsometer as defined in claim 27, wherein the linear polarized light source comprises a laser light source and a linear polarizing device.

31. The ellipsometer as defined in claim 27, wherein the phase modulator is a feed-back control system with liquid crystal therein.

32. The ellipsometer as defined in claim 27, wherein the reference analyzer comprises a non-polarizing beam splitter and a detector.

33. The ellipsometer as defined in claim 27, wherein the polarization analyzer comprises a polarizing beam splitter and a detector.

34. An ellipsometer for measuring the complex refractive index and thin film thickness of a sample through a transparent or translucent medium, comprising:

a linear polarized light source used to generate a measuring beam for detecting the sample;

a phase modulator used to control the phase of the measuring beam thereby to generate a sampling beam;

a reference analyzer used to generate a reference beam according part of the sampling beam to adjust the intensity of the sampling beam;

a polarization analyzer used to analyze the phase, polarization and intensity of the sampling beam after the sampling beam is reflected by the sample; and a light direction controller used to control the incident angle and direction of the sampling beam with respect to the sample, wherein the sampling beam is reflected by the sample to enter the light direction controller through the medium, and thereafter the sampling beam is reflected by the light direction controller to pass through the medium and re-reflected by the sample to enter the polarization analyzer along an original optical path, but toward an opposite direction, wherein the light direction controller comprises:

a prism used to reflect the sampling beam thereby to turn the sampling beam by 90°;

a concave quasi-parabolic cylindrical mirror used to reflect the sampling beam coming from the prism to enter the sample through the medium, wherein the incident angle of the sampling beam with respect to the measurement area of the sample can be changed when the prism moves up and down;

a concave quasi-cylindrical mirror used to perpendicularly reflect the sampling beam coming from the sample back to the sample through the medium; and a feed-back control two-dimension stage used to determine the measurement area of the sample.

35. The ellipsometer as defined in claim 34, wherein the linear polarized light source is a laser light source which can emit a linear polarized light.

36. The ellipsometer as defined in claim 34, wherein the linear polarized light source comprises a non-coherent light source and a linear polarizing device.

37. The ellipsometer as defined in claim 34, wherein the linear polarized light source comprises a laser light source and a linear polarizing device.

38. The ellipsometer as defined in claim 34, wherein the phase modulator is a feed-back control system with liquid crystal therein.

39. The ellipsometer as defined in claim 34, wherein the reference analyzer comprises a non-polarizing beam splitter and a detector.

40. The ellipsometer as defined in claim 34, wherein the polarization analyzer comprises a polarizing beam splitter and a detector.

41. An ellipsometer for measuring the complex refractive index of a sample and thin film thickness through a transparent or translucent medium, comprising:

a linear polarized light source used to generate a measuring beam for detecting the sample;

a phase modulator used to control the phase of the measuring beam thereby to generate a sampling beam;

a reference analyzer used to generate a reference beam according to part of the sampling beam to adjust the intensity of the sampling beam;

a polarization analyzer used to analyze the phase, polarization and intensity of the sampling beam after the sampling beam is reflected by the sample;

a light direction controller used to control the incident angle and direction of the sampling beam with respect to the sample, wherein the sampling beam is reflected by the sample to enter the light direction controller through the medium, and thereafter the sampling beam is reflected by the light direction controller to pass through the medium and re-reflected by the sample to enter the polarization analyzer along an original optical path, but toward an opposite direction; and an ellipsomeric parameter calibrator used to replace the sample to allow the sampling beam be perpendicularly incident to the surface of the ellipsomeric parameter calibrator and perpendicularly reflected when the ellipsomeric parameters of the phase modulator, the reference analyzer, the polarization analyzer and the medium are calibrated.

42. The ellipsometer as defined in claim 41, wherein the linear polarized light source is a laser light source which can emit a linear polarized light.

43. The ellipsometer as defined in claim 41, wherein the linear polarized light source comprises of a non-coherent light source and a linear polarizing device.

44. The ellipsometer as defined in claim 41, wherein the linear polarized light source comprises a laser light source and a linear polarizing device.

45. The ellipsometer as defined in claim 41, wherein the phase modulator is a feed-back control system with liquid crystal therein.

46. The ellipsometer as defined in claim 41, wherein the reference analyzer comprises a non-polarizing beam splitter and a detector.

47. The ellipsometer as defined in claim 41, wherein the polarization analyzer comprises a polarizing beam splitter and a detector.

48. The ellipsometer as defined in claim 41, wherein the light direction controller comprises:
  a prism used to refract the sampling beam thereby to turn the sampling beam by 90°;
  a concave quasi-paraboloidal mirror used to reflect the sampling beam coming from the prism to enter the sample through the medium, wherein the incident angle of the sampling beam with respect to the measurement point of the sample can be changed when the prism moves up and down;
  a concave quasi-spherical mirror used to perpendicularly reflect the sampling beam coming from the sample back to the sample through the medium; and
  a feed-back control two-dimension stage used to determine the measurement point of the sample.

49. The ellipsometer as defined in claim 41, wherein the light direction controller comprises:
  a prism used to refract the sampling beam thereby to turn the sampling beam by 90°;
  a concave quasi-parabolic cylindrical mirror used to reflect the sampling beam coming from the prism to enter the sample through the medium, wherein the incident angle of the sampling beam with respect to the measurement area of the sample can be changed when the prism moves up and down;
  a concave quasi-cylindrical mirror used to perpendicularly reflect the sampling beam coming from the sample back to the sample through the medium; and
  a feed-back control two-dimension stage used to determine the measurement area of the sample.

50. The ellipsometer as defined in claim 41, wherein the ellipsomeric parameter calibrator uses a convex quasi-spherical mirror to replace the sample thereby to make the sampling beam be perpendicularly incident to the convex spherical mirror when calibration is performed.

51. The ellipsometer as defined in claim 41, wherein the ellipsomeric parameter calibrator use a planar mirror that is gradually adjusted according to the incident angle of the sampling beam to ensure that the incident beam is perpendicularly incident to the planar mirror when calibration is performed.

52. The ellipsometer as defined in claim 41, wherein the ellipsomeric parameter calibrator uses a standard sample with known ellipsomeric parameters for calibration.

* * * * *